United States Patent
Hiramitsu et al.

(10) Patent No.: US 8,993,749 B2
(45) Date of Patent: Mar. 31, 2015

(54) ERIOCITRIN-CONTAINING MATERIAL, METHOD FOR PRODUCTION OF THE ERIOCITRIN-CONTAINING MATERIAL, AND FOOD, BEVERAGE, PHARMACEUTICAL PREPARATION AND COSMETIC EACH COMPRISING THE ERIOCITRIN-CONTAINING MATERIAL

(75) Inventors: Masanori Hiramitsu, Komaki (JP); Toshikazu Omori, Aichi (JP); Kenji Yamaguchi, Ichinomiya (JP); Hiroaki Bessho, Inuyama (JP)

(73) Assignee: Pokka Corporation, Aichi (JP)

( * ) Notice: Subject to any disclaimer, the term of this patent is extended or adjusted under 35 U.S.C. 154(b) by 873 days.

(21) Appl. No.: 12/740,331

(22) PCT Filed: Dec. 26, 2008

(86) PCT No.: PCT/JP2008/073681
§ 371 (c)(1),
(2), (4) Date: Apr. 28, 2010

(87) PCT Pub. No.: WO2009/084612
PCT Pub. Date: Jul. 9, 2009

(65) Prior Publication Data
US 2010/0256079 A1 Oct. 7, 2010

(30) Foreign Application Priority Data

Dec. 27, 2007 (JP) ................................. 2007-337778

(51) Int. Cl.
| | | |
|---|---|---|
| *C07H 1/06* | (2006.01) | |
| *C07H 1/08* | (2006.01) | |
| *A01N 43/04* | (2006.01) | |
| *A61K 31/70* | (2006.01) | |
| *A61K 31/7048* | (2006.01) | |
| *A61K 8/49* | (2006.01) | |
| *A61K 36/752* | (2006.01) | |
| *A61Q 19/00* | (2006.01) | |
| *C07H 17/07* | (2006.01) | |

(52) U.S. Cl.
CPC ............. *A61K 31/7048* (2013.01); *A61K 8/498* (2013.01); *A61K 36/752* (2013.01); *A61Q 19/00* (2013.01); *C07H 17/07* (2013.01)
USPC ............................................ 536/127; 514/27

(58) Field of Classification Search
CPC . A61K 8/498; A61K 31/7048; A61K 36/752; A61Q 19/00; C07H 17/07
USPC ............................................. 536/127; 514/27
See application file for complete search history.

(56) References Cited

U.S. PATENT DOCUMENTS 6,350,477 B1    2/2002  Yamamoto et al.

FOREIGN PATENT DOCUMENTS

| EP | 1 166 643 A1 * | 1/2002 | ................ A23J 3/14 |
|---|---|---|---|
| JP | 09-048969 | 2/1997 | |
| JP | 10-245552 | 9/1998 | |
| JP | 2000-217560 | 8/2000 | |
| JP | 2001011333 A | 1/2001 | |
| JP | 2001-204425 | 7/2001 | |
| JP | 2002-029975 | 1/2002 | |
| JP | 2005087166 A | 4/2005 | |
| JP | 2005-225847 | 8/2005 | |
| JP | 2007-112852 | 5/2007 | |

OTHER PUBLICATIONS

"Decolorization" by Advanced Biosciences (2005).*
"Duolite® A7" by Rohm and Haas Company (1996).*
"PCT International Preliminary Report on Patentability" for the International Application No. PCT/JP2008/073681, as issued by The International Bureau of WIPO on Aug. 10, 2010.

* cited by examiner

*Primary Examiner* — Scarlett Goon
(74) *Attorney, Agent, or Firm* — Seager, Tufte & Wickhem LLC

(57) ABSTRACT

A process for producing an eriocitrin-containing material comprises the steps of: preparing an eriocitrin-containing citrus extract from a citrus fruit using an extractant; and separating eriocitrin from the citrus extract. The step of separating eriocitrin from the citrus extract comprises the steps of: bringing the citrus extract into contact with a porous synthetic adsorption resin such that eriocitrin in the citrus extract is adsorbed on the porous synthetic adsorption resin, the porous synthetic adsorption resin comprising a phenol-formaldehyde resin as a main framework and having amino and phenolic hydroxyl groups; and eluting the eriocitrin adsorbed on the porous synthetic adsorption resin using an elution solvent.

6 Claims, No Drawings

ERIOCITRIN-CONTAINING MATERIAL, METHOD FOR PRODUCTION OF THE ERIOCITRIN-CONTAINING MATERIAL, AND FOOD, BEVERAGE, PHARMACEUTICAL PREPARATION AND COSMETIC EACH COMPRISING THE ERIOCITRIN-CONTAINING MATERIAL

FIELD OF THE INVENTION

The present invention relates to a material containing eriocitrin derived from a citrus, which is favorably used in, for example, food or drink products, pharmaceuticals, and cosmetics, and to a process for producing the same.

BACKGROUND OF THE INVENTION

Citrus fruits are known to be rich in antioxidants, such as eriocitrin, 6,8-di-C-glucosyldiosmetin, and 6-C-glucosyldiosmetin, belonging to polyphenols. These antioxidants derived from natural materials can be utilized favorably in various industrial products such as food or drink products, pharmaceuticals, and cosmetics. These antioxidants can be extracted from citrus fruits according to previously known processes described in Patent Documents 1 to 3.

Patent Documents 1 and 2 respectively describe a process for producing a polyphenol-containing material, which comprises purifying, using reverse-phase resin treatment or liquid chromatography, an extract obtained from a citrus material using water, an organic solvent, or a mixed solvent thereof.

Patent Document 3 describes a process for producing a food material containing eriocitrin at a high concentration. The process described in Patent Document 3 comprises: obtaining an extract from at least one of juices, peels, and squeezed residue of citrus fruits using an extractant; applying the extract to a porous synthetic adsorption resin such that eriocitrin is adsorbed on this resin; for the removal of impurities, washing, with water, the synthetic adsorption resin comprising the eriocitrin adsorbed thereon; and then separating and recovering the eriocitrin adsorbed on the synthetic adsorption resin using an organic solvent.

The production processes described in Patent Documents 1 and 2 involve fractionation based on high-performance liquid chromatography for enhancing polyphenol purity in the obtained polyphenol-containing material. However, this procedure, which is complicated and time-consuming, results in increase in the cost of producing the polyphenol-containing material. Alternatively, the production process described in Patent Document 3 involves, for the removal of impurities, washing, with water, the synthetic adsorption resin comprising the eriocitrin adsorbed thereon. However, foods supplemented with the obtained eriocitrin-containing material, particularly, foods supplemented with this material at a high concentration, still have bitterness or other unpleasant tastes and leave unpleasant aftertaste in the mouth after being ingested. The eriocitrin-containing material produced by the process described in Patent Document 3 has a peculiar, Chinese herbal medicine-like smell (crude drug smell) attributed to heat applied in extraction, concentration, and purification steps. In addition, general polyphenol-containing materials tend to have offensive smells or browning due to changes over time. Thus, their long-term quality maintenance is difficult to attain.

Patent Document 1: Japanese Laid-Open Patent Publication No. 9-48969
Patent Document 2: Japanese Laid-Open Patent Publication No. 10-245552
Patent Document 3: Japanese Laid-Open Patent Publication No. 2000-217560

SUMMARY OF THE INVENTION

An objective of the present invention is to provide a material containing eriocitrin derived from a citrus, which has low contents of components responsible for deterioration in the quality of the eriocitrin-containing material, to provide a process for producing such an eriocitrin-containing material, and to provide a food or drink product, a pharmaceutical, and a cosmetic comprising such an eriocitrin-containing material formulated therein.

To achieve the objective, a first aspect of the present invention provides an eriocitrin-containing material which is obtained by separating eriocitrin from an eriocitrin-containing citrus extract prepared from a citrus fruit using an extractant. The eriocitrin separation from the citrus extract is carried out by: bringing the citrus extract into contact with a porous synthetic adsorption resin such that eriocitrin in the citrus extract is adsorbed on the porous synthetic adsorption resin, the porous synthetic adsorption resin comprising a phenol-formaldehyde resin as a main framework and having amino and phenolic hydroxyl groups; and then eluting the eriocitrin adsorbed on the porous synthetic adsorption resin using an elution solvent.

A second aspect of the present invention provides a food or drink product comprising the eriocitrin-containing material according to the first aspect formulated therein.

A third aspect of the present invention provides a pharmaceutical comprising the eriocitrin-containing material according to the first aspect formulated therein.

A fourth aspect of the present invention provides a cosmetic comprising the eriocitrin-containing material according to the first aspect formulated therein.

A fifth aspect of the present invention provides a process for producing an eriocitrin-containing material, which comprises the steps of: preparing an eriocitrin-containing citrus extract from a citrus fruit using an extractant; and separating eriocitrin from the citrus extract. The step of separating eriocitrin from the citrus extract comprises the steps of: bringing the citrus extract into contact with a porous synthetic adsorption resin such that eriocitrin in the citrus extract is adsorbed on the porous synthetic adsorption resin, the porous synthetic adsorption resin comprising a phenol-formaldehyde resin as a main framework and having amino and phenolic hydroxyl groups; and eluting the eriocitrin adsorbed on the porous synthetic adsorption resin using an elution solvent.

DETAILED DESCRIPTION OF THE PREFERRED EMBODIMENTS

Hereinafter, one embodiment of the present invention will be described. An eriocitrin-containing material of the present embodiment contains, at a high concentration, eriocitrin having excellent antioxidant effects. This eriocitrin-containing material is mainly added for use to, for example, food or drink products, pharmaceuticals, and cosmetics. The eriocitrin-containing material is produced using citrus fruits as a raw material. The eriocitrin-containing material is preferably composed mainly of eriocitrin. The phrase "composed mainly of eriocitrin" means that an eriocitrin content occupies the highest percentage of soluble solid matter in the eriocitrin-containing material. The eriocitrin content is preferably 20% by weight or higher, more preferably 50% by weight or higher, in the soluble solid matter.

Eriocitrin, also called eriodictyol-7-rutinoside, is a flavonoid glycoside where rutinose (L-rhamnosyl-D-glucose) is bound with eriodictyol ($C_{15}H_{12}O_6$; also called 3',4',5,7-tetrahydroxyflavanone) belonging to flavanones, a group of flavonoids.

Examples of the citrus fruits used as a raw material for the eriocitrin-containing material include fruits of flavorful acid citruses (e.g., lemon (*Citrus limon*), lime (*Citrus aurantifolia*), *Citrus depressa, Citrus sudachi, Citrus junos*, bitter orange (*Citrus aurantium*), and *Citrus sphaerocarpa*), grapefruit (*Citrus paradisi*), navel orange (*Citrus sinensis* var. *brasiliensis*), Valencia orange (*Citrus sinensis* cv. *Valencia*), sour orange, *Citrus hassaku, Citrus unshiu, Citrus iyo, Citrus reticulata, Citrus natsudaidai Hayata* f. *Kawanonatsudaidai*, and *pomelo* (*Citrus maxima* or *Citrus grandis*). Among them, fruits of lemon and lime which are especially rich in eriocitrin are preferable. The eriocitrin-containing material contains eriocitrin derived from one or more of these citrus fruits.

Eriocitrin is contained in a large amount in peels of citrus fruits. In this context, the citrus fruits encompass peels, juices, pulp segments, juice sacs, and seeds. The peels of citrus fruits contain, in addition to eriocitrin, odorous components responsible for peculiar, Chinese herbal medicine-like smells (crude drug smells), taste components responsible for bitterness or other unpleasant tastes, and colored components responsible for generation of turbidity or apparent reduction in freshness. These odorous, taste, and colored components are generally extracted easily together with eriocitrin from the peels of citrus fruits using, for example, water or alcohol.

The eriocitrin-containing material of the present embodiment is reduced in peculiar, Chinese herbal medicine-like smells caused by heat applied in extraction, concentration, and purification steps and offensive smells caused by changes over time. Therefore, the eriocitrin-containing material is suitably used in food or drink products, cosmetics, and pharmaceuticals having dosage forms for oral or transnasal administration. Moreover, the eriocitrin-containing material, when orally ingested, hardly offers bitterness or other unpleasant tastes and hardly leaves unpleasant aftertaste in the mouth. Therefore, the eriocitrin-containing material is particularly suitably used in food or drink products and pharmaceuticals having dosage forms for oral administration.

The eriocitrin-containing material is produced by, first, obtaining an eriocitrin-containing citrus extract from citrus fruits (or portions thereof). When portions of the citrus fruits are used as a raw material, peels or squeezed residue of the citrus fruits are preferable. In this case, a citrus extract rich in eriocitrin is easily obtained. The squeezed residue is residue left after the squeezing of juices from the citrus fruits. This residue contains peels, pulp segments, a portion of juice sacs, seeds, and an exceedingly small amount of unsqueezed juices. When the squeezed residue is used as a raw material, exocarp (flavedo) is preferably removed. To improve the extraction efficiency, raw material is preferably fractionized in advance, for example, through cutting, pulverizing, or grinding. For example, a food processor may be used to fractionize the raw material.

The citrus extract is obtained from the citrus fruits using an organic solvent or water as an extractant. The organic solvent may be a polar solvent, for example, alcohol (e.g., methanol, ethanol, butanol, propanol, and isopropanol), glycerin, or glacial acetic acid or may be a nonpolar solvent, for example, hexane or ethyl acetate. The extractant may be used alone or in combination of two or more of the solvents. When the eriocitrin-containing material is added for use to food or drink products, pharmaceuticals, and cosmetics, water or ethanol is preferable from the viewpoint of applicability, the cost of producing the eriocitrin-containing material, and eriocitrin extraction efficiency. The extraction temperature (temperature of the extractant) is not particularly limited and may be room temperature, for example, 5 to 45° C. The extraction may be carried out under either static or stirring conditions. The extraction time is preferably 30 minutes or longer for extracting a sufficient amount of eriocitrin. For enhancing eriocitrin extraction efficiency and enhancing the clarity of the obtained citrus extract, pectinase may also be added into the extractant to accomplish the degradation of pectin contained in the raw material, simultaneously with eriocitrin extraction.

The citrus extract thus obtained from the citrus fruits is subjected to solid-liquid separation for removal of solid matter contained in the obtained citrus extract. The solid-liquid separation may be carried out using a method known in the art, such as centrifugation or membrane separation. Centrifugation is preferable because of its convenience. Prior to the solid-liquid separation using centrifugation or membrane separation, large solid matter such as peels may be removed in advance from the citrus extract by mesh filtration or decantation. The citrus extract (extract solution) thus separated from solid matter by removal based on the solid-liquid separation is concentrated or diluted with water, if necessary. The concentration of the citrus extract may be carried out using a method known in the art, such as vacuum concentration, membrane concentration, or freeze concentration. When ethanol is used as the extractant and has a concentration exceeding 20% by volume in the citrus extract, the citrus extract is preferably concentrated or diluted with water to adjust the ethanol concentration therein to 20% by volume or lower.

The citrus extract thus separated from solid matter by removal based on the solid-liquid separation is concentrated or diluted with water, if necessary, and then subjected to eriocitrin separation using a particular porous synthetic adsorption resin. Specifically, a phenol-formaldehyde adsorption resin (first porous synthetic adsorption resin) comprising a phenol-formaldehyde resin as a main framework and having amino and phenolic hydroxyl groups as functional groups is used, and the citrus extract is brought into contact with the phenol-formaldehyde adsorption resin such that eriocitrin contained in the citrus extract is adsorbed on the phenol-formaldehyde adsorption resin. Then, the eriocitrin adsorbed on the phenol-formaldehyde adsorption resin is eluted using an elution solvent to obtain an eriocitrin fraction. Eriocitrin is not only physically adsorbed onto the surface of the phenol-formaldehyde adsorption resin but also chemically and ion-exchange adsorbed by the action of the amino group which is a weakly basic group and the phenolic hydroxyl group which is a weakly acidic group in the phenol-formaldehyde adsorption resin in acidic and neutral regions. General porous synthetic adsorption resins have a larger pore size (several tens to several hundreds of angstroms) than that of active carbon and can thus adsorb thereon substances having a relatively large molecular size. The phenol-formaldehyde adsorption resin may be, for example, either HOKUETSU HS or HOKUETSU KS manufactured by Ajinomoto Fine-Techno Co., Inc.

The contact of the citrus extract with the phenol-formaldehyde adsorption resin is carried out by applying the citrus extract to the phenol-formaldehyde adsorption resin packed in a column. The phenol-formaldehyde adsorption resin thus brought into contact with the citrus extract is preferably washed.

The washing of the phenol-formaldehyde adsorption resin is intended to remove impurities other than eriocitrin from the phenol-formaldehyde adsorption resin and is carried out by pouring a washing solvent to the phenol-formaldehyde adsorption resin in the column thus brought into contact with the citrus extract. The washing solvent preferably does not elute the eriocitrin adsorbed on the phenol-formaldehyde adsorption resin. Specifically, the washing solvent may be water or an organic solvent, which may be the same as that used as the extractant. The washing solvent is brought into contact with the phenol-formaldehyde adsorption resin such that some impurities are eluted into the washing solvent whereas the eriocitrin remains through adsorption in the phenol-formaldehyde adsorption resin without being eluted into the washing solvent. This is because in the presence of the washing solvent, the adsorption of some impurities on the phenol-formaldehyde adsorption resin is weaker than the adsorption of the eriocitrin thereon. The temperature of the washing solvent is not particularly limited and may be room temperature, for example, 5 to 40° C. However, the temperature of the washing solvent is preferably 40 to 100° C. for removing impurities more efficiently. When hydrous alcohol is used as the washing solvent, the washing solvent preferably has an alcohol concentration of 20% by volume or lower for reducing the elution of the eriocitrin adsorbed on the phenol-formaldehyde adsorption resin into the washing solvent.

The elution of the eriocitrin adsorbed on the phenol-formaldehyde adsorption resin using the elution solvent is carried out by washing, if necessary, the phenol-formaldehyde adsorption resin in the column thus brought into contact with the citrus extract and then pouring an elution solvent to the phenol-formaldehyde adsorption resin. As a result, an eriocitrin fraction, that is, an eriocitrin eluate is obtained. The elution solvent that is used for eluting the eriocitrin adsorbed on the phenol-formaldehyde adsorption resin may be an organic solvent, for example, alcohol (e.g., methanol, ethanol, butanol, propanol, and isopropanol), acetone, hexane, chloroform, glycerin, or glacial acetic acid or may be water. The elution solvent may be used alone or in combination of two or more of the solvents. When the eriocitrin-containing material is added for use to food or drink products, pharmaceuticals, and cosmetics, ethanol or water is preferable from the viewpoint of applicability, the cost of producing the eriocitrin-containing material, and eriocitrin recovery efficiency. When hydrous ethanol is used as the elution solvent, the elution solvent preferably has an ethanol concentration of 20 to 90% by volume, more preferably 40 to 85% by volume, particularly preferably 60 to 80% by volume. In the elution solvent having an ethanol concentration of 20% by volume or higher, the eriocitrin adsorbed on the phenol-formaldehyde adsorption resin is eluted particularly efficiently. In the elution solvent having an ethanol concentration of 90% by volume or lower, components responsible for deterioration in the flavor of the eriocitrin-containing material are eluted in much lower amounts.

The eriocitrin eluate thus obtained may be used as the eriocitrin-containing material either directly or after being concentrated, dried, or diluted with water, if necessary. The concentration and drying of the eriocitrin eluate may be carried out using a method known in the art, such as vacuum concentration, membrane concentration, freeze concentration, vacuum drying, or freeze drying.

The citrus extract before being subjected to the eriocitrin separation using the phenol-formaldehyde adsorption resin may be subjected to eriocitrin separation using another porous synthetic adsorption resin, if necessary. Alternatively, the eriocitrin eluate obtained by subjecting the citrus extract to the eriocitrin separation using the phenol-formaldehyde adsorption resin may be subjected to eriocitrin separation using another porous synthetic adsorption resin. In either case, higher quality of the eriocitrin-containing material and a higher eriocitrin content in the eriocitrin-containing material are achieved. Preferably, the eriocitrin separation using another porous synthetic adsorption resin that is different from the phenol-formaldehyde adsorption resin is carried out prior to the eriocitrin separation using the phenol-formaldehyde adsorption resin. The eriocitrin separation using another porous synthetic adsorption resin that is different from the phenol-formaldehyde adsorption resin is carried out using a porous synthetic adsorption resin (second porous synthetic adsorption resin) comprising at least one selected from styrenic and acrylic adsorption resins. Specifically, the citrus extract or the eriocitrin eluate is brought into contact with the second porous synthetic adsorption resin such that the eriocitrin contained in the citrus extract or the eriocitrin eluate is adsorbed on the second porous synthetic adsorption resin. Then, the eriocitrin adsorbed on the second porous synthetic adsorption resin is eluted using an elution solvent to obtain an eriocitrin fraction.

The second porous synthetic adsorption resin may be, for example, any of DUOLITE S-861, DUOLITE ES-865, AMBERLITE XAD-4, AMBERLITE XAD-7, and AMBERLITE XAD-16 all manufactured by Rohm and Haas Co. or any of DIAION HP20, DIAION HP2MG, SEPABEADS SP207, SEPABEADS SP700, and SEPABEADS SP825 all manufactured by Mitsubishi Chemical Corp.

The contact of the citrus extract or the eriocitrin eluate with the second porous synthetic adsorption resin is carried out by applying the citrus extract or the eriocitrin eluate to the second porous synthetic adsorption resin packed in a column. The second porous synthetic adsorption resin thus brought into contact with the citrus extract or the eriocitrin eluate is preferably washed.

The washing of the second porous synthetic adsorption resin is intended to remove impurities other than eriocitrin from the second porous synthetic adsorption resin and is carried out by pouring a washing solvent to the second porous synthetic adsorption resin in the column thus brought into contact with the citrus extract or the eriocitrin eluate. The washing solvent preferably does not elute the eriocitrin adsorbed on the second porous synthetic adsorption resin. Specifically, the washing solvent may be water or an organic solvent, which may be the same as that used as the extractant. The temperature of the washing solvent is not particularly limited and may be room temperature, for example, 5 to 40° C. However, the temperature of the washing solvent is preferably 40 to 100° C. for removing impurities more efficiently. When hydrous alcohol is used as the washing solvent, the washing solvent preferably has an alcohol concentration of 20% by volume or lower for reducing the elution of the eriocitrin adsorbed on the second porous synthetic adsorption resin into the washing solvent.

The elution of the eriocitrin adsorbed on the second porous synthetic adsorption resin using the elution solvent is also carried out by washing, if necessary, the second porous synthetic adsorption resin in the column thus brought into contact with the citrus extract or the eriocitrin eluate and then pouring an elution solvent to the second porous synthetic adsorption resin. As a result, an eriocitrin fraction, that is, an eriocitrin eluate is obtained. The elution solvent that is used for eluting the eriocitrin adsorbed on the second porous synthetic adsorption resin may be an organic solvent, for example, alcohol (e.g., ethanol), acetone, hexane, chloroform, glycerin, or glacial acetic acid or may be water. The elution solvent may be used alone or in combination of two or more of the solvents. When the eriocitrin-containing material is added for use to food or drink products, pharmaceuticals, and cosmetics, ethanol or water is preferable from the viewpoint of applicability, the cost of producing the eriocitrin-containing material, and eriocitrin recovery efficiency. When hydrous ethanol is used as the elution solvent, the elution solvent preferably has an ethanol concentration of 20 to 50% by volume, more preferably 30 to 40% by volume. In the elution solvent having an ethanol concentration of 20% by volume or higher, the eriocitrin adsorbed on the second porous synthetic adsorption resin is eluted particularly efficiently. In the elution solvent having an ethanol concentration of 50% by volume or lower, components responsible for deterioration in the flavor of the eriocitrin-containing material are eluted in much lower amounts.

The eriocitrin eluate obtained by subjecting the citrus extract to the eriocitrin separation using the second porous synthetic adsorption resin may subsequently be subjected to eriocitrin separation using the phenol-formaldehyde adsorption resin. In this case, when the eriocitrin eluate subjected to eriocitrin separation using the phenol-formaldehyde adsorption resin has an ethanol concentration exceeding 20% by volume, the eriocitrin eluate is preferably diluted or concentrated in advance to adjust the ethanol concentration therein to 20% by volume or lower. Alternatively, the eriocitrin eluate obtained by subjecting the citrus extract to the eriocitrin separation using the phenol-formaldehyde adsorption resin may subsequently be subjected to eriocitrin separation using the second porous synthetic adsorption resin. In this case, when the eriocitrin eluate applied to the second porous synthetic adsorption resin has an ethanol concentration exceeding 20% by volume, the eriocitrin eluate is preferably diluted or concentrated in advance to adjust the ethanol concentration therein to 20% by volume or lower.

The eriocitrin-containing material of the present embodiment is mainly formulated for use in, for example, food or drink products (e.g., drinks, alcoholic drinks, foods, healthy foods, healthy drinks, and nutritional supplements), pharmaceuticals, quasi drugs, pharmaceuticals for animals, feed, and cosmetics, for exhibiting in vivo the excellent antioxidant effects of eriocitrin.

Examples of the food or drink products in which the eriocitrin-containing material can be formulated include: soft drinks such as black tea, barley tea, green tea, oolong tea, blend tea, wild grass tea, herb tea, coffee, fruit juice drink, vegetable drink, cocoa, soybean milk, sports drink, carbonated drink, and milk drink; confectionery such as candies, biscuits, and snacks; and alcoholic drinks such as cocktail, white liquor highball, sour, beer, and wine. The eriocitrin-containing material can also be formulated in other foods containing a gelling agent such as pectin or carrageenan or in various seasonings. The food or drink product comprising the eriocitrin-containing material formulated therein may further contain additives, such as sugars (e.g., glucose, sucrose, fructose, lactose, dextrin, dietary fiber, and polysaccharides), acidulants, flavors, sweeteners (e.g., stevia, aspartame, and sugar alcohol), coloring agents, stabilizers, vitamins, amino acids, various minerals, and plant or animal fat and oil, appropriately formulated therein without impairing the advantages of the present invention.

When the eriocitrin-containing material is used as a pharmaceutical, the eriocitrin-containing material can be administered not only by oral administration but also by other various methods such as intravascular and transdermal administrations. The dosage form of the eriocitrin-containing material that is used as a pharmaceutical is not particularly limited and may be, for example, powders, dusting powders, granules, tablets, capsules, pills, suppositories, solutions, or injections. The eriocitrin-containing material that is used as a pharmaceutical may further contain additives, such as excipients, bases, emulsifiers, solvents, or stabilizers, formulated therein.

According to the present embodiment, advantages shown below can be obtained.

In the present embodiment, the eriocitrin separation from the citrus extract is carried out using the phenol-formaldehyde adsorption resin comprising a phenol-formaldehyde resin as a main framework and having amino and phenolic hydroxyl groups. Therefore, components derived from peels, etc. of citrus fruits, such as odorous, bitter, and colored components, responsible for deterioration in the quality of the eriocitrin-containing material are removed efficiently. Thus, the obtained eriocitrin-containing material is of high quality and contains eriocitrin at a high concentration. More specifically, the eriocitrin-containing material obtained in the present embodiment hardly has offensive smells, increased bitterness and astringency, or browning caused by changes over time and is excellently stable over time.

In the present embodiment, the eriocitrin adsorbed on the phenol-formaldehyde adsorption resin is eluted using the hydrous ethanol having an ethanol concentration of 20 to 90% by volume. This permits efficient removal of components responsible for deterioration in the flavor and appearance of the eriocitrin-containing material, while permitting efficient eriocitrin elution and recovery.

In the present embodiment, prior to or following the eriocitrin separation using the phenol-formaldehyde adsorption resin, the step of separating eriocitrin is preferably carried out using the second porous synthetic adsorption resin comprising at least one selected from styrenic and acrylic adsorption resins. This permits more efficient separation or removal of components responsible for deterioration in the flavor and appearance of the eriocitrin-containing material and permits a further higher eriocitrin content in the eriocitrin-containing material.

The eriocitrin-containing material obtained in the present embodiment can be formulated in food or drink products, pharmaceuticals, and cosmetics, and such food or drink products, pharmaceuticals, and cosmetics have smell, taste, and color of high quality, in spite of the high concentration of eriocitrin contained therein. Therefore, they are consecutively ingested or used easily.

When squeezed residue left after the squeezing of juices from citrus fruits is used as a raw material for the eriocitrin-containing material, a large amount of the eriocitrin-containing citrus extract can be obtained extremely easily. The squeezed residue of citrus fruits is generated in a large amount from the production of drink products containing citrus fruit juice. Thus, it can be obtained at low cost. Further, the reuse of the squeezed residue of citrus fruits is advantageous from the viewpoint of Food Recycling Law.

The embodiment may be changed or modified as follows.

The eriocitrin separation using the phenol-formaldehyde adsorption resin is not only carried out once but also may be repeated twice or more. Likewise, the eriocitrin separation using the porous synthetic adsorption resin comprising at least one selected from styrenic and acrylic adsorption resins is not only carried out once but also may be repeated twice or more. In this case, further removal of impurities is achieved.

The form of the eriocitrin-containing material is not particularly limited and may be, for example, a liquid or powder form.

Next, the present invention will be described further specifically with reference to Examples and Comparative Examples.

Production of Eriocitrin-Containing Material

Example 1

2 kg of squeezed residue of lemon was pulverized, and this pulverized material was dipped in 10 L of water as an extractant and left standing at room temperature for 30 minutes to obtain a lemon extract solution. The obtained lemon extract solution was mesh-filtrated (mesh size: 500 μm/32 mesh) and then centrifuged at 9,000 rpm for 20 minutes. The supernatant after centrifugation was subjected to ultrafiltration at a molecular weight cut off of 20,000 to obtain a clear filtrate (crude extract solution).

The obtained filtrate was applied to a column packed with 200 ml of a phenol-formaldehyde adsorption resin (HOKUETSU HS manufactured by Ajinomoto Fine-Techno Co., Inc.). Then, 600 ml of water and 600 ml of hydrous ethanol having an ethanol concentration of 10% by volume were poured as washing solvents in order to the column to wash the phenol-formaldehyde adsorption resin. Subsequently, 1 L of hydrous ethanol having an ethanol concentration of 80% by volume was poured as an elution solvent to the column to elute eriocitrin adsorbed on the phenol-formaldehyde adsorption resin. The eluate thus obtained was vacuum-concentrated for ethanol removal to obtain an eriocitrin-containing material of Example 1.

Example 2

Water was added to the eriocitrin-containing material obtained in Example 1 to prepare 2 L of a solution, which was in turn applied to a column packed with 200 ml of a styrenic adsorption resin (AMBERLITE XAD-16 manufactured by Rohm and Haas Co.). Then, 600 ml of water and 600 ml of hydrous ethanol having an ethanol concentration of 10% by volume were poured as washing solvents in order to the column to wash the styrenic adsorption resin. Subsequently, 1 L of hydrous ethanol having an ethanol concentration of 40% by volume was poured as an elution solvent to the column to elute the eriocitrin adsorbed on the styrenic adsorption resin. The eluate thus obtained was vacuum-concentrated for ethanol removal to obtain an eriocitrin-containing material of Example 2.

Example 3

2 kg of squeezed residue of lemon was pulverized, and this pulverized material was dipped in 10 L of water as an extractant and left standing at room temperature for 30 minutes to obtain a lemon extract solution. The obtained lemon extract solution was mesh-filtrated (mesh size: 500 μm/32 mesh) and then centrifuged at 9000 rpm for 20 minutes. The supernatant after centrifugation was subjected to ultrafiltration at a molecular weight cut off of 20,000 to obtain a clear filtrate (crude extract solution).

The obtained filtrate was applied to a column packed with 200 ml of a phenol-formaldehyde adsorption resin (HOKUETSU HS manufactured by Ajinomoto Fine-Techno Co., Inc.). Then, 600 ml of water and 600 ml of hydrous ethanol having an ethanol concentration of 10% by volume were poured as washing solvents in order to the column to wash the phenol-formaldehyde adsorption resin. Subsequently, 1 L of hydrous ethanol having an ethanol concentration of 40% by volume was poured as an elution solvent to the column to elute eriocitrin adsorbed on the phenol-formaldehyde adsorption resin. The eluate thus obtained was vacuum-concentrated for ethanol removal to obtain an eriocitrin-containing material of Example 3.

Example 4

Water was added to the eriocitrin-containing material obtained in Example 3 to prepare 2 L of a solution, which was in turn applied to a column packed with 200 ml of a styrenic adsorption resin (AMBERLITE XAD-16 manufactured by Rohm and Haas Co.). Then, 600 ml of water and 600 ml of hydrous ethanol having an ethanol concentration of 10% by volume were poured as washing solvents in order to the column to wash the styrenic adsorption resin. Subsequently, 1 L of hydrous ethanol having an ethanol concentration of 40% by volume was poured as an elution solvent to the column to elute the eriocitrin adsorbed on the styrenic adsorption resin. The eluate thus obtained was vacuum-concentrated for ethanol removal to obtain an eriocitrin-containing material of Example 4.

Comparative Example 1

An eriocitrin-containing material was obtained by the same procedures as in Example 1 except that a styrenic adsorption resin (AMBERLITE XAD-16 manufactured by Rohm and Haas Co.) was used instead of the phenol-formaldehyde adsorption resin and that hydrous ethanol having an ethanol concentration of 40% by volume was used as an elution solvent instead of the hydrous ethanol having an ethanol concentration of 80% by volume.

Example 5

Water was added to the eriocitrin-containing material obtained in Comparative Example 1 to prepare 2 L of a solution, which was in turn applied to a column packed with 200 ml of a phenol-formaldehyde adsorption resin (HOKUETSU HS manufactured by Ajinomoto Fine-Techno Co., Inc.). Then, 600 ml of water and 600 ml of hydrous ethanol having an ethanol concentration of 10% by volume were poured as washing solvents in order to the column to wash the phenol-formaldehyde adsorption resin. Subsequently, 1 L of hydrous ethanol having an ethanol concentration of 40% by volume was poured as an elution solvent to the column to elute the eriocitrin adsorbed on the phenol-formaldehyde adsorption resin. The eluate thus obtained was vacuum-concentrated for ethanol removal to obtain an eriocitrin-containing material of Example 5.

Example 6

Water was added to the eriocitrin-containing material obtained in Comparative Example 1 to prepare 2 L of a solution, which was in turn applied to a column packed with 200 ml of a phenol-formaldehyde adsorption resin (HOKUETSU HS manufactured by Ajinomoto Fine-Techno Co., Inc.). Then, 600 ml of water and 600 ml of hydrous ethanol having an ethanol concentration of 10% by volume were poured as washing solvents in order to the column to wash the phenol-formaldehyde adsorption resin. Subsequently, 1 L of hydrous ethanol having an ethanol concentration of 80% by volume was poured as an elution solvent to the column to elute the eriocitrin adsorbed on the phenol-formaldehyde adsorption resin. The eluate thus obtained was vacuum-concentrated for ethanol removal to obtain an eriocitrin-containing material of Example 6.

Comparative Example 2

Water was added to the eriocitrin-containing material obtained in Comparative Example 1 to prepare 2 L of a solution, which was in turn applied to a column packed with 200 ml of a styrenic adsorption resin (AMBERLITE XAD-16). Then, 600 ml of water and 600 ml of hydrous ethanol having an ethanol concentration of 10% by volume were poured as washing solvents in order to the column to wash the styrenic adsorption resin. Subsequently, 1 L of hydrous ethanol having an ethanol concentration of 40% by volume was poured as an elution solvent to the column to elute the eriocitrin adsorbed on the styrenic adsorption resin. The eluate thus obtained was vacuum-concentrated for ethanol removal to obtain an eriocitrin-containing material of Comparative Example 2.

Comparative Example 3

The clear filtrate (crude extract solution) obtained in Example 1 was applied to a column packed with 200 ml of a phenol-formaldehyde adsorption resin (AMBERLITE XAD-761 manufactured by Rohm and Haas Co.). Then, 1 L of hydrous ethanol having an ethanol concentration of 40% by volume was poured as an elution solvent to the column to elute the eriocitrin adsorbed on the phenol-formaldehyde adsorption resin. The eluate thus obtained was vacuum-concentrated for ethanol removal to obtain an eriocitrin-containing material of Comparative Example 3. In this context, the AMBERLITE XAD-761 has a phenol-formaldehyde resin as a main framework and phenolic hydroxyl and methylol groups as ion-exchange groups and has an average pore size of 600 angstroms.

Quality Evaluation on Eriocitrin-Containing Materials

The eriocitrin-containing materials of Examples 1 to 6 and Comparative Examples 1 to 3 were adjusted to the equal eriocitrin concentration of 1,800 ppm determined using high-performance liquid chromatography (HPLC). They were separately measured for absorbance at a wavelength of 420 nm and Brix values of soluble solid matter concentrations and further evaluated for flavor. The absorbance measurement was carried out using a double-beam spectrophotometer U-2000 model manufactured by Hitachi, Ltd. The flavor evaluation was carried out by evaluating crude drug smells and bitterness by sensory assessment on a 7-point scale of −, ±, +, ++, +++, ++++, and +++++. The larger number of + represents stronger crude drug smells or bitterness. The measurement and evaluation results are shown in Table 1.

TABLE 1

| Classification | Eriocitrin (ppm) | Brix | Eriocitrin/Brix | Absorbance (420 nm) | Flavor Crude drug smell | Bitterness |
|---|---|---|---|---|---|---|
| Example 1 | 1,800 | 2.5 | 720 | 1.082 | ++ | +++ |
| Example 2 | 1,800 | 0.9 | 2,000 | 1.073 | + | ++ |
| Example 3 | 1,800 | 1.1 | 1,636 | 1.080 | + | ++ |
| Example 4 | 1,800 | 0.8 | 2,250 | 1.014 | ± | + |
| Example 5 | 1,800 | 0.6 | 3,000 | 0.448 | ± | ± |
| Example 6 | 1,800 | 0.8 | 2,250 | 0.604 | + | + |
| Comparative Example 1 | 1,800 | 1.3 | 1,385 | 2.253 | ++++ | ++++ |
| Comparative Example 2 | 1,800 | 1.3 | 1,385 | 1.690 | +++ | +++ |
| Comparative Example 3 | 1,800 | 1.4 | 1,286 | 2.587 | ++ | ++ |

The results shown in Table 1 demonstrated the followings.

The eriocitrin-containing material of Example 1 obtained using the phenol-formaldehyde adsorption resin (HOKUETSU HS) was confirmed to have better flavor and less coloring than those of the eriocitrin-containing material of Comparative Examples 1 and 2 obtained using only the styrenic adsorption resin (AMBERLITE XAD-16).

The eriocitrin-containing material of Example 2 obtained using the phenol-formaldehyde adsorption resin and subsequently the styrenic adsorption resin (AMBERLITE XAD-16) was confirmed to have much better flavor and much less coloring.

The eriocitrin-containing material of Example 2 was confirmed, as can be seen from the large eriocitrin/Brix value, to have a higher eriocitrin content by virtue of the removal of impurities.

The eriocitrin-containing materials of Examples 3 and 4 obtained using hydrous ethanol having a relatively low ethanol concentration for eluting the eriocitrin adsorbed on the phenol-formaldehyde adsorption resin (HOKUETSU HS) was confirmed to have more favorable flavor, less coloring, and a larger eriocitrin/Brix value than those of the eriocitrin-containing materials of Examples 1 and 2 obtained using hydrous ethanol having a relatively high ethanol concentration.

The eriocitrin-containing material of Comparative Example 3 obtained using the phenol-formaldehyde adsorption resin (AMBERLITE XAD-761) that is different from the phenol-formaldehyde adsorption resin having amino and phenolic hydroxyl groups was confirmed to be insufficiently reduced in coloring.

The eriocitrin-containing materials of Comparative Examples 1 and 2 obtained using the styrenic adsorption resin instead of the phenol-formaldehyde adsorption resin had unfavorable flavor, insufficiently reduced coloring, and a small eriocitrin/Brix value. By contrast, the eriocitrin-containing materials of Examples 5 and 6 obtained using the styrenic adsorption resin and subsequently the phenol-formaldehyde adsorption resin (HOKUETSU HS) had better flavor, less coloring, and a higher eriocitrin/Brix value.

In conclusion, it is evident that an eriocitrin-containing material of high quality having favorable flavor and color is obtained by using the phenol-formaldehyde adsorption resin having amino and phenolic hydroxyl groups.

Production of Lemon-Flavored Drink Containing Eriocitrin-Containing Material

Example 7

70 g of sucrose and 2 g of trisodium citrate were formulated in 20 g of clear concentrated lemon juice (Brix 40). The eriocitrin-containing material obtained in Example 2 was added thereto at a final eriocitrin concentration of 600 ppm, and water was added to prepare 1 L of a solution. This solution was sterilized at 85° C. for 30 seconds and then hot-packed in bottles in an amount of 100 mL/bottle to obtain a lemon-flavored drink of Example 7. The obtained lemon-flavored drink was left standing at 60° C. for 3 days for accelerated changes over time. Then, the lemon-flavored drink was measured for absorbance at a wavelength of 420 nm and further evaluated for flavor. The flavor evaluation was carried out by evaluating offensive smells and bitterness by sensory assessment on a 7-point scale of −, ±, +, ++, +++, ++++, and +++++. The larger number of + represents stronger offensive smells or bitterness. The measurement and evaluation results are shown in Table 2.

Comparative Example 4

70 g of sucrose and 2 g of trisodium citrate were formulated in 20 g of clear concentrated lemon juice (Brix 40). The eriocitrin-containing material obtained in Comparative Example 2 was added thereto at a final eriocitrin concentration of 600 ppm, and water was added to prepare 1 L of a solution. This solution was sterilized at 85° C. for 30 seconds and then hot-packed in bottles in an amount of 100 mL/bottle to obtain a lemon-flavored drink of Comparative Example 4. The obtained lemon-flavored drink was left standing at 60° C. for 3 days for accelerated changes over time. Then, the lemon-flavored drink was subjected to absorbance measurement and flavor evaluation in the same way as in the lemon-flavored drink of Example 7. The results are shown in Table 2.

TABLE 2

| Classification | Absorbance (420 nm) | Flavor Offensive smell | Bitterness |
|---|---|---|---|
| Example 7 | 0.317 | + | + |
| Comparative Example 4 | 0.451 | +++ | ++ |

As shown in Table 2, the lemon-flavored drink of Example 7 was confirmed to have less coloring or deterioration in flavor caused by changes over time than the lemon-flavored drink of Comparative Example 4.

Study on Elution Solvent

When producing the eriocitrin-containing material of Example 1, instead of using the hydrous ethanol having an ethanol concentration of 80% by volume as elution solvent, the eriocitrin adsorbed on the phenol-formaldehyde adsorption resin was eluted by sequentially increasing the ethanol concentration of the elution solvent, that is, by sequentially using, as elution solvent, hydrous ethanol having an ethanol concentration of 10% by volume, hydrous ethanol having an ethanol concentration of 20% by volume, hydrous ethanol having an ethanol concentration of 30% by volume, hydrous ethanol having an ethanol concentration of 40% by volume, hydrous ethanol having an ethanol concentration of 60% by volume, hydrous ethanol having an ethanol concentration of 80% by volume, and 100% ethanol. The resultant eriocitrin-containing materials, which were obtained for each ethanol concentration of elution solvent, were adjusted to the equal eriocitrin concentration of 1800 ppm. They were separately measured for absorbance at a wavelength of 420 nm and Brix values of soluble solid matter concentrations and further evaluated for flavor. Moreover, each clear filtrate (crude extract solution) before being applied to the column packed with the phenol-formaldehyde adsorption resin (HOKUETSU HS) was measured for eriocitrin contents using HPLC. Based on the contents, eriocitrin recovery rates were determined. The flavor evaluation was carried out by evaluating crude drug smells and bitterness by sensory assessment on a 7-point scale of −, ±, +, ++, +++, ++++, and +++++. The larger number of + represents stronger crude drug smells or bitterness. The measurement and evaluation results are shown in Table 3.

TABLE 3

| Elution solvent | Eriocitrin (ppm) | Brix | Eriocitrin/ Brix | Absorbance (420 nm) | Flavor Crude drug smell | Bitterness | Eriocitrin recovery rate |
|---|---|---|---|---|---|---|---|
| 10% by volume of ethanol | 1,800 | 2.1 | 857 | 0.700 | − | ± | 5.8% |
| 20% by volume of ethanol | 1,800 | 1.9 | 947 | 0.648 | ± | + | 20.4% |
| 30% by volume of ethanol | 1,800 | 1.4 | 1,286 | 1.000 | ± | + | 40.6% |
| 40% by volume of ethanol | 1,800 | 1.1 | 1,636 | 1.080 | + | ++ | 49.0% |
| 60% by volume of ethanol | 1,800 | 1.8 | 1,000 | 1.136 | + | ++ | 73.2% |
| 80% by volume of ethanol | 1,800 | 2.5 | 720 | 1.082 | ++ | +++ | 80.0% |
| 100% ethanol | 1,800 | 2.6 | 692 | 1.372 | +++ | ++++ | 86.1% |

As shown in Table 3, the lower ethanol concentration in the elution solvent was confirmed to tend to provide less coloring and better flavor in the obtained eriocitrin-containing material. Moreover, the higher ethanol concentration in the elution solvent was confirmed to tend to provide a higher eriocitrin recovery rate. However, too low an ethanol concentration or too high an ethanol concentration in the elution solvent was also confirmed, as can be seen from the small eriocitrin/Brix value, to result in insufficient removal of impurities. Thus, all things considered, the ethanol concentration in the elution solvent was demonstrated to be particularly preferably 60 to 80% by volume. When HOKUETSU KS manufactured by Ajinomoto Fine-Techno Co., Inc. was used as a phenol-formaldehyde adsorption resin instead of HOKUETSU HS, the same results were also obtained (data not shown).

The invention claimed is:

1. A process for producing an eriocitrin-containing material, comprising the steps of:
preparing an eriocitrin-containing citrus extract from a citrus fruit using an extractant; and
separating eriocitrin from the citrus extract, wherein the step of separating eriocitrin from the citrus extract comprises the steps of:
bringing the citrus extract into contact with a porous synthetic adsorption resin such that eriocitrin in the citrus extract is adsorbed on the porous synthetic adsorption resin, the porous synthetic adsorption resin comprising a phenol-formaldehyde resin as a main framework and having amino and phenolic hydroxyl groups; and
eluting the eriocitrin adsorbed on the porous synthetic adsorption resin using an elution solvent to obtain an eluate containing the eriocitrin, wherein the elution solvent is hydrous ethanol having an ethanol concentration of 60-80% by volume.

2. The process for producing an eriocitrin-containing material according to claim 1, wherein the step of separating eriocitrin from the citrus extract further comprises bringing the eluate into contact with the porous synthetic adsorption resin again, followed by eluting the adsorbed eriocitrin from the porous synthetic adsorption resin.

3. The process for producing an eriocitrin-containing material according to claim 1, wherein the porous synthetic adsorption resin and the elution solvent are a first porous synthetic adsorption resin and a first elution solvent, respectively, and wherein the step of separating eriocitrin from the citrus extract further comprises:
bringing the eluate into contact with a second porous synthetic adsorption resin such that the eriocitrin in the eluate is adsorbed on the second porous synthetic adsorption resin, the second porous synthetic adsorption resin comprising at least one selected from styrenic and acrylic adsorption resins; and
eluting the eriocitrin adsorbed on the second porous synthetic adsorption resin using a second elution solvent.

4. The process for producing an eriocitrin-containing material according to claim 3, wherein the second elution solvent is hydrous ethanol having an ethanol concentration of 20 to 50% by volume.

5. A process for producing an eriocitrin-containing material, comprising the steps of:
preparing an eriocitrin-containing citrus extract from a citrus fruit using an extractant; and
separating eriocitrin from the citrus extract, wherein the step of separating the eriocitrin from the citrus extract comprises:
bringing the citrus extract into contact with a second porous synthetic adsorption resin such that eriocitrin in the citrus extract is adsorbed on the second porous synthetic adsorption resin, the second porous synthetic adsorption resin comprising at least one selected from styrenic and acrylic adsorption resins;
eluting the eriocitrin adsorbed on the second porous synthetic adsorption resin using a second elution solvent to obtain an eluate containing the eriocitrin;
bringing the eluate into contact with a first porous synthetic adsorption resin such that the eriocitrin in the eluate is adsorbed on the first porous synthetic adsorption resin, the first porous synthetic adsorption resin comprising a phenol-formaldehyde resin as a main framework and having amino and phenolic hydroxyl groups; and
eluting the eriocitrin adsorbed on the first porous synthetic adsorption resin using a first elution solvent, wherein the first elution solvent is hydrous ethanol having an ethanol concentration of 60-80% by volume.

6. The process for producing an eriocitrin-containing material according to claim 5, wherein the second elution solvent is hydrous ethanol having an ethanol concentration of 20 to 50% by volume.

* * * * *